United States Patent [19]

MacDonald Stuart G.

[11] Patent Number: 4,846,192

[45] Date of Patent: Jul. 11, 1989

[54] REARWARDLY ACTING SURGICAL CATHETER

[75] Inventor: MacDonald Stuart G., Pultneyville, N.Y.

[73] Assignee: Eastman Kodak Company, Rochester, N.Y.

[21] Appl. No.: 39,346

[22] Filed: Apr. 17, 1987

[51] Int. Cl.$^4$ .............................................. A61B 6/00
[52] U.S. Cl. ..................................... 128/752; 604/22
[58] Field of Search ....................... 604/22, 267, 280; 128/305, 311, 318, 750.3, 757, 758

[56] References Cited

U.S. PATENT DOCUMENTS

| | | | |
|---|---|---|---|
| 769,829 | 9/1904 | Mott | 128/311 |
| 2,708,437 | 5/1955 | Hutchins | 128/311 |
| 3,173,414 | 3/1965 | Guillant | 128/318 |
| 3,448,741 | 6/1969 | Dennis et al. | |
| 3,732,858 | 5/1973 | Banko | 604/22 |
| 3,886,943 | 6/1975 | Skiff et al. | |
| 4,020,847 | 5/1977 | Clark, III | 128/751 |
| 4,273,128 | 6/1981 | Lary | |
| 4,290,427 | 9/1981 | Chin | |
| 4,315,511 | 2/1982 | Chin | |
| 4,512,344 | 4/1985 | Barber | |
| 4,559,927 | 12/1985 | Chin | |
| 4,574,781 | 3/1986 | Chin | |
| 4,620,547 | 11/1986 | Boebel | |
| 4,621,636 | 11/1986 | Fogarty | |
| 4,669,469 | 6/1987 | Gifford et al. | |
| 4,685,458 | 8/1987 | Leckrone | |

FOREIGN PATENT DOCUMENTS

| | | | |
|---|---|---|---|
| 584856 | 12/1977 | U.S.S.R. | |
| 2018601 | 10/1979 | United Kingdom | 604/22 |

OTHER PUBLICATIONS

Clinica, "Innovations in Endoscopy", Timonth Tankosic, M.D., Jul. 1987.

Primary Examiner—Stephen C. Pellegrino
Assistant Examiner—Colleen Reilly
Attorney, Agent, or Firm—Dana M. Schmidt

[57] ABSTRACT

A surgical catheter is disclosed, comprising a distal end for advancing into a blood vessel at a single incision remote from occlusions, a proximal end for manipulating the catheter ex vivo, a body portion connecting the two ends, and means adjacent the distal end for cutting away such occlusions while the distal end is far removed from the incision, the cutting means including at least a movable cutting edge. The catheter is improved in that the movable cutting edge is disposed so that it faces rearwardly, towards the body portion. Further there is included means for moving the cutting edge rearwardly to cut tissue or fatty deposits towards the catheter body portion and the remote incision.

Such a catheter is used in a surgical method such that the cutting means is activated to cut the fatty deposits only in a rearward direction towards the incision, instead of in an advancing direction.

1 Claim, 1 Drawing Sheet

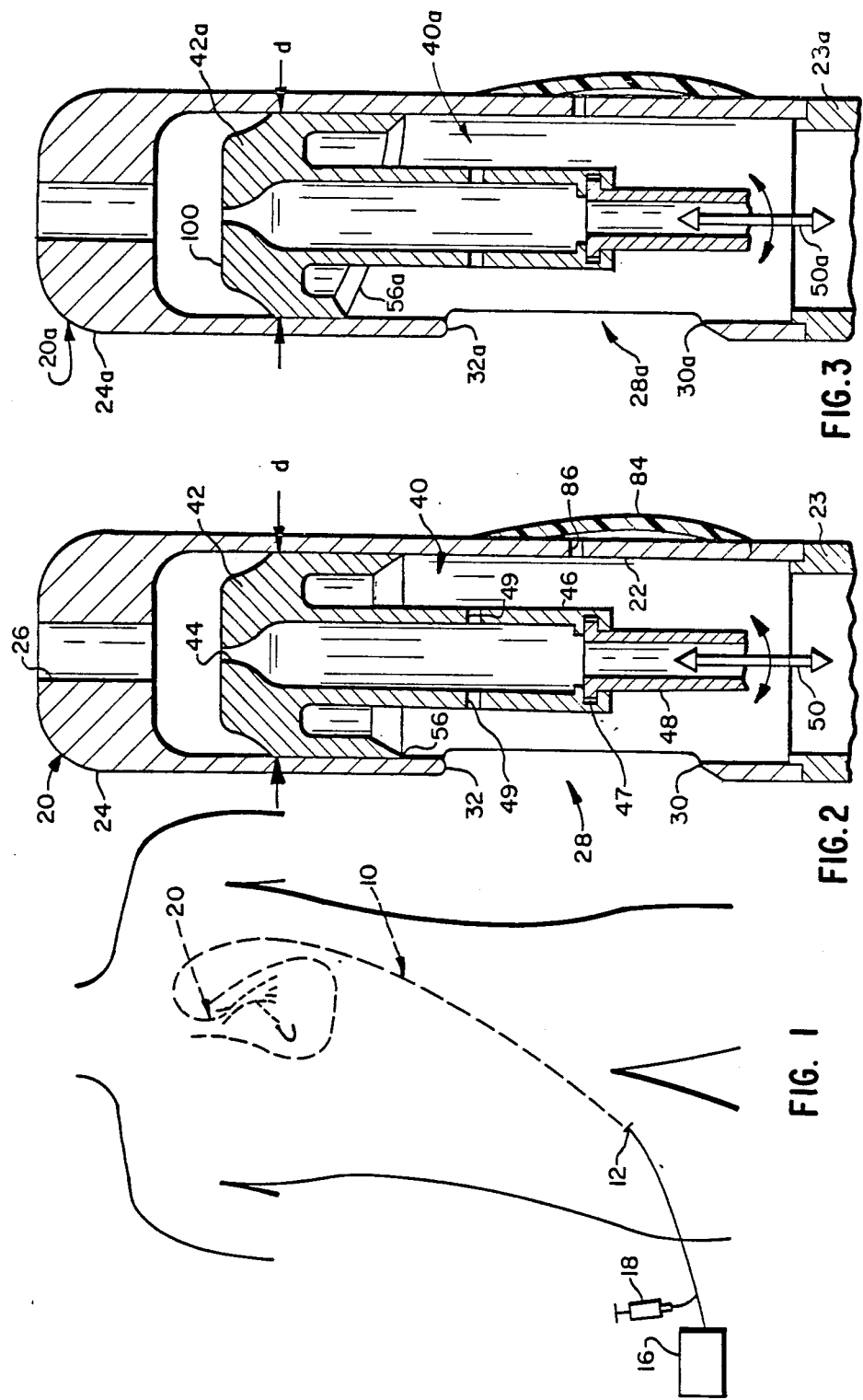

REARWARDLY ACTING SURGICAL CATHETER

FIELD OF THE INVENTION

This invention relates to surgical catheters used to cut and remove obstructions in vessels such as arteries and the like, by being inserted into incisions that are remote from the obstructions.

BACKGROUND OF THE INVENTION

Cutting catheters are known in the art, in which an arterial or endarterectomy catheter has at its distal end, a cutting surface that cuts away fatty deposits. Invariably, however, such catheters cut while being pushed forward. Examples of such catheters are shown in the following: U.S. Pat. Nos. 3,448,741; 4,273,128; and 4,512,344. A disadvantage with such devices is that the continued removal of material in front of the catheter can lead to a build-up of debris that clogs the artery or catheter, so as to render further progress difficult. Another disadvantage is that cutting catheters that cut while advancing, occasionally run into curvatures in the vessel wall that cause the cutting surface to injure the vessel inadvertently. Even if a shield is provided in front of the cutting means, the problem is that when the cutting means cuts towards the shield, it builds up deposits within the catheter, requiring repeated withdrawal for cleaning.

SUMMARY OF THE INVENTION

I have devised a surgical catheter that avoids the problems noted above, encountered by the prior art catheters that cut by moving away from the incision used to insert them.

More specifically, in accord with one aspect of the invention there is provided a surgical catheter comprising a distal end for advancing into a blood vessel at a single incision remote from occlusions, a proximal end for manipulating the catheter ex vivo, a body portion connecting the two ends, and means adjacent the distal end for cutting away such occlusions while the distal end is far removed from the incision, the cutting means including at least a movable cutting edge. The catheter is improved in that the movable cutting edge is disposed so that it faces rearwardly, towards the body portion, and also in that there is further included means for moving the cutting edge rearwardly to cut tissue or fatty deposits towards the body portion and the remote incision.

In accord with another aspect of the invention, there is provided such a catheter wherein the cutting means includes a pair of mechanical cutting edges and means for moving the edges together to provide a shearing action, one of the edges being stationary relative to the body portion of the catheter, and the other movable relative to the stationary edge. The catheter is improved in that the movable cutting edge is disposed to face rearwardly to cut only while the cutting edge is pulled rearwardly towards the body portion.

In accord with a further aspect of the invention, there is provided a method for removing fatty deposits from occlusions in blood vessels using a catheter having a distal end, a proximal end, a body portion connecting the ends, and cutting means on the distal end for cutting away the fatty deposits. The method comprises the steps of forming an incision in such blood vessel at a location remote from such occlusions, inserting the distal end and body portion into the incision, advancing the distal end and body portion towards an occlusion while retaining the proximal end ex vivo, positioning the distal end over such occlusion, and pulling one of the cutting means rearwardly towards the body portion to cut the occlusion.

Thus it is an advantageous feature of the invention that the catheter cuts loose the fatty deposits in a direction that favors withdrawal of them out of the artery. This avoids a build-up of deposits in the catheter that can occur if the cutting action is in the opposite direction, as provided in certain prior catheters.

It is a related advantageous feature of the invention that such a catheter need not be withdrawn after just a few cuts, because the distal end has not become clogged with deposits.

Other advantageous features will become apparent upon reference to the following description of the preferred embodiments, when read in light of the attached drawings.

BRIEF DESCRIPTION OF THE DRAWINGS

FIG. 1 is a schematic illustration of the use of a catheter constructed in accord with the invention, to cut away deposits at locations remote from the incision used to insert the catheter;

FIG. 2 is a section view of the distal end of the catheter illustrating its inventive features; and FIG. 3 is a section view similar to that of FIG. 2, but of an alternate embodiment.

DESCRIPTION OF THE PREFERRED EMBODIMENTS

The invention is described hereinafter in connection with its use in cutting away fatty deposits in an artery, a preferred embodiment. In addition, the invention is useful in catheters used to cut away thickened atheromatous tunica intima, usually fatty deposits, of any body channel, whether or not it is an artery.

FIG. 1 illustrates the manner in which a catheter 10 constructed in accordance with the invention is inserted in an incision 12 in a patient's body, and pushed along an artery such as the femoral artery until it reaches an occlusion, here shown as being in the coronary artery C. That occlusion is remote from the incision, as is the distal end 20 of the catheter. Control of the catheter is achieved ex vivo by control means 16, as is conventional.

Distal end 20, FIG. 2, comprises a cylindrical tube 22 connected in a conventional manner to a flexible body 23 of the catheter (which extends back to the incision and to control means 16), and a movable member 40 mounted within tube 22 for movement relative to the tube. To protect the vessel walls while the catheter is advancing through the curvilinear body vessel, tube 22 further preferably comprises shield portion 24 apertured at 26 for additional features hereinafter discussed, and cutting aperture 28. Such aperture has a knife edge 30 that faces forwardly towards the shield portion. Opposite edge 32 of aperture 28 is either a sharp cutting edge, or it can be blunt, since it does not cooperate with the moving member 40 for a shearing action.

Member 40 comprises an end portion 42 having an exterior diameter "d" that permits a sliding fit within the interior walls of cylindrical body 22, and a hollow interior passageway 44. That passageway is part of a sleeve 46 that has a reduced exterior diameter compared to diameter d. Sleeve 46 is then connected at 47 to a hollow tube 48 that extends all the way back through body portion 23 of the catheter. Tube 48 is hollow to allow the flow of, e.g., blood through the catheter and hence through the artery during the operation. Openings 49 are provided in sleeve 46 for aiding in removing cut material. Tube 48 and its connected sleeve 46 and end portion 42 are moved relative to tube 22, (arrow 50) either in a reciprocating fashion, a rotating fashion, or both, by hand or by a conventional, preferably reciprocating motor in control 16, FIG. 1.

To provide shearing action to the distal portion 20, end portion 42 terminates in an annular cutting edge 56 that faces only rearwardly and which cooperates with stationary cutting edge 30 to shear off fatty deposits that get caught in aperture 28. Edge 56 is the active cutting edge, since without it edge 30 does substantially no cutting, as is intended. Member 40 acts to cut while it is being pulled rearwardly, so that the cut fatty deposits are directed rearwardly towards body portion 23. To assist in the steady removal of the cut deposits, a wash liquid preferably is pumped towards distal end 20 through tube 48. It exits at apertures 49. (If necessary, aperture 44 can be eliminated to insure flow out of apertures 49.) At the same time, a suction is applied from control 16 to pull liquid and the cut debris down towards the incision, through body portion 23. During this phase of the operation, the patient's blood will not flow through tube 48 or body portion 23, but it is conventional for the catheter diameter to permit blood flow around the outside.

Optionally, a conventional balloon 84 can be mounted on the side of tube 22 opposite to aperture 28, to be expanded by a liquid delivered out through aperture 86 from a feeder line, not shown. Such a balloon is used to push distal end 20 towards the occlusion so that aperture 28 surrounds a portion of it.

Shield aperture 26 can be used to allow blood to continue flowing through the artery, or it can be used for a flexible probe (not shown) that extends beyond shield 24, particularly if greater flexibility is desired than is possible with distal portion 20. Alternatively, it can be used for injection of a dye that is sent down the catheter from a syringe 18, FIG. 1, through the hollow tube 48.

In the alternative embodiment of FIG. 3, the cutting edge of the moving part need not be annular as in the previous embodiment. Parts similar to those previously described bear the same reference numerals to which the distinguishing suffix "a" is appended. Thus, distal portion 20a comprises shield 24a, aperture 28a, and cutting edge 30a, constructed as in the previous embodiment. However, cutting edge 56a is formed so as to have a spiral locus, measured from end surface 100 of end 42a of member 40a, that is continuously variable around the circumference of edge 56a. This shape provides greater shearing as member 40a is reciprocated (arrow 50a) relative to tube 22a. (Preferably, member 40a is not rotated.) As in the previous embodiment, cutting occurs only in a direction towards the incision.

In use, the catheter is controlled at the proximal end ex vivo, as is conventional. The distal end is pushed to the occlusions to be operated on, preferably while member 40 is pulled back to a position blocking aperture 28, to shield edge 30 from snagging on the vessel wall. Then end 20 is moved over against an occlusion while member 40 is pushed forwardly, opening up aperture 28. When a part of the occlusion is projecting into aperture 28, member 40 is reciprocated so that it cuts (shears) back towards the incision to cause severing of fatty deposits. These deposits are then pulled rearwardly out body portion 23, with or without the aid of a wash liquid.

Techniques such as control of bleeding are readily achieved by conventional methods, some of which are discussed in, e.g., U.S. Pat. No. 4,273,128.

Because of the invention, buildup of removed fatty deposits does not occur when using this catheter. Furthermore, removal of such severed parts is readily achieved.

The invention has been described in detail with particular reference to preferred embodiments thereof, but it will be understood that variations and modifications can be effected within the spirit and scope of the invention.

What is claimed is:

1. A method for removing fatty deposits from occlusions in blood vessels using a catheter having a distal end sized to fit into blood vessels, a proximal end, a flexible body portion connecting said ends, and cutting means on said distal end for cutting away such fatty deposits;

the method comprising the steps of forming an incision in such blood vessel at a location remote from such occlusions, inserting said distal end and body portion into the incision, advancing said distal end and body portion towards such occlusion by flexing said body portion while retaining said proximal end ex vivo, positioning said distal end over an occlusion, pulling one of said cutting means rearwardly towards said body portion to cut said occlusion, and creating a partial vaccum within said distal end to remove deposits cut from said occlusion, out through said body portion, without withdrawing said distal end from the site of the occlusion.

* * * * *

UNITED STATES PATENT AND TRADEMARK OFFICE
CERTIFICATE OF CORRECTION

PATENT NO. : 4,846,192
DATED : July 11, 1989
INVENTOR(S) : Stuart G. MacDonald

It is certified that error appears in the above-identified patent and that said Letters Patent is hereby corrected as shown below:

Column 4, line 50 should read: --creating a partial vacuum within said distal end to--

Signed and Sealed this

Fifteenth Day of January, 1991

*Attest:*

HARRY F. MANBECK, JR.

*Attesting Officer*     *Commissioner of Patents and Trademarks*